United States Patent
Burton

(10) Patent No.: US 11,000,333 B2
(45) Date of Patent: May 11, 2021

(54) ANGULAR OPTICAL FIBER CATHETER

(71) Applicant: The Spectranetics Corporation, Colorado Springs, CO (US)

(72) Inventor: George Woodrow Burton, Colorado Springs, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 19 days.

(21) Appl. No.: 13/800,864

(22) Filed: Mar. 13, 2013

(65) Prior Publication Data
US 2014/0276695 A1 Sep. 18, 2014

(51) Int. Cl.
- *A61B 18/24* (2006.01)
- *G02B 6/04* (2006.01)
- *A61B 18/22* (2006.01)

(52) U.S. Cl.
CPC ........... *A61B 18/24* (2013.01); *G02B 6/04* (2013.01); *A61B 2018/2211* (2013.01); *Y10T 29/49826* (2015.01)

(58) Field of Classification Search
CPC ... A61B 18/24; A61B 2018/2211; G02B 6/04; Y10T 29/49826
USPC .................................. 385/123–128; 606/2–19
See application file for complete search history.

(56) References Cited

U.S. PATENT DOCUMENTS

| | | | | |
|---|---|---|---|---|
| 4,716,287 A * | 12/1987 | Nestler | ......... | G06F 3/0317 250/221 |
| 4,758,064 A * | 7/1988 | Neefe | ......... | B29D 11/00663 264/1.24 |
| 6,157,763 A * | 12/2000 | Grubb | ......... | G02B 6/03622 372/6 |
| 6,201,915 B1 * | 3/2001 | Rizkin | ......... | G02B 6/0006 362/554 |
| 7,251,399 B2 * | 7/2007 | Kuo | ......... | G02B 6/1221 385/114 |
| 2004/0207894 A1 * | 10/2004 | Hodges | ......... | H04J 14/02 359/223.1 |
| 2008/0108981 A1 * | 5/2008 | Telfair | ......... | A61B 18/24 606/4 |
| 2009/0067793 A1 * | 3/2009 | Bennett | ......... | C03B 37/0122 385/125 |
| 2009/0163899 A1 * | 6/2009 | Burton | ......... | A61B 18/24 606/15 |
| 2009/0173334 A1 * | 7/2009 | Krs | ......... | F24J 2/42 126/569 |
| 2010/0182405 A1 * | 7/2010 | Monteiro | ......... | G02B 6/04 348/45 |
| 2012/0069861 A1 * | 3/2012 | Neuberger | ......... | G02B 6/02 372/6 |
| 2012/0274559 A1 * | 11/2012 | Mathai | ......... | G02B 6/04 345/158 |
| 2013/0170806 A1 * | 7/2013 | Denner | ......... | G02B 6/0001 385/129 |

* cited by examiner

*Primary Examiner* — Rex R Holmes

(57) ABSTRACT

A laser catheter assembly is provided that includes a plurality of laser active fibers, each fiber having a substantially non-circular fiber cross-section.

8 Claims, 6 Drawing Sheets

ANGULAR OPTICAL FIBER CATHETER

FIELD

The disclosure relates generally to catheters and particularly to laser catheters.

BACKGROUND

Laser energy can be transmitted through optical fibers housed in a relatively flexible tubular catheter inserted into a body lumen, such as a blood vessel, ureter, fallopian tube, cerebral artery and the like to remove obstructions in the lumen. Catheters used for laser angioplasty and other procedures can have a central passage or tube which receives a guide wire inserted into the body lumen (e.g., vascular system) prior to catheter introduction. The guide wire facilitates the advancement and placement of the catheter to the selected portion(s) of the body lumen for laser ablation of tissue.

The optical fibers directing the laser light to the catheter tip are generally circular in cross section and therefore have a relatively low packing density. Packing density in the coupler, or optical connector between the catheter and laser system, is generally directly proportional to coupling efficiency and the durability of the proximal pack. Accordingly, it is generally desirable to have as high an optical fiber packing density as possible.

SUMMARY

These and other needs are addressed by the various aspects, embodiments, and configurations of the present disclosure. The present disclosure is directed to the use of angular or planar optical fibers to provide relatively high levels of packing density, particularly the use of such angular or planar optical fibers in a laser catheter to focus the amount of optical energy that the fibers emit into a smaller laser active area of the optical fiber, thereby increasing substantially the catheter's laser ablation capability.

A laser catheter assembly, according to this disclosure, can include a plurality of laser active fibers, each fiber having a substantially non-circular or non-arcuate fiber cross-section.

A laser catheter assembly, according to this disclosure can include a plurality of laser active fibers. One or more of the following can be true:
  (a) a cladding material thickness "$A_j$" of each of the laser active fibers is no less than about 2.5 microns, generally at or adjacent to a corner of a laser active core of the fibers;
  (b) each laser active fiber has one or more substantially angular corners; and
  (c) each laser active fiber has one or more substantially planar and/or flat edges.

A manufacturing method, according to this disclosure, can include the step of assembling or closely packing a plurality of laser active fibers to provide a laser catheter assembly.

An active core of the fiber can have a flat-to-flat thickness ranging from about 50 to about 200 microns.

The packing density of a laser catheter assembly is normally measured at or adjacent to a distal and/or proximal end of the catheter, depending on the catheter assembly configuration. The distal end normally refers to the portion of the catheter assembly adjacent to the coupler. As defined below, the coupler couples the distal end of the catheter assembly to the laser.

The packing density of the laser catheter assembly can also be measured at the distal end of the laser catheter assembly in certain catheter assembly configurations, particularly a laser ablation lumenless catheter assembly having densely packed laser emitters at the distal end.

The present disclosure can provide a number of advantages depending on the particular configuration. The non-circular optical fibers can enable relatively high packing densities, thereby providing relatively high coupling efficiencies and a more durable proximal pack. For a given fluence and wavelength, the non-circular fibers can emit a smaller laser beam compared to circular lasers, thereby providing a higher calcium ablation ability. The non-circular optical fibers can have acceptable fiber energy losses, higher calcium penetration abilities, and flexibility characteristics.

These and other advantages will be apparent from the disclosure of the aspects, embodiments, and configurations contained herein.

"Angular" is a shape having one or more angles.

"Arcuate" is a shape that is shaped like an arc or curve. A non-arcuate shape may be have an arcuate portion but also has an angular or planar portion.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

A "laser emitter" refers to an end portion of a fiber or an optical component that emits laser light from a distal end of the catheter towards a desired target, which is typically tissue.

A "catheter" is a tube that can be inserted into a body cavity, duct, lumen, or vessel, such as the vasculature system. In most uses, a catheter is a thin, flexible tube ("soft" catheter), though in some uses, it may be a larger, solid, less flexible—but possibly still flexible—catheter ("hard" catheter).

"Circular" refers to a curved shape. A non-circular shape may have a circular portion but also has an angular or planar portion.

"Coronary catheterization" is a generally minimally invasive procedure to access the coronary circulation and/or blood filled chambers of the heart using a catheter. It is performed for both diagnostic and interventional (treatment) purposes.

A "coupler" or "fiber optic coupler" refers to the optical fiber device with one or more input fibers and one or several output fibers. Fiber couplers are commonly special optical fiber devices with one or more input fibers for distributing optical signals into two or more output fibers. Optical energy is passively split into multiple output signals (fibers), each containing light with properties identical to the original except for reduced amplitude. Fiber couplers have input and output configurations defined as M×N. M is the number of input ports (one or more). N is the number of output ports and is always equal to or greater than M. Fibers can be thermally tapered and fused so that their cores come into intimate contact. This can also be done with polarization-maintaining fibers, leading to polarization-maintaining couplers (PM couplers) or splitters. Some couplers use side-polished fibers, providing access to the fiber core. Couplers can also be made from bulk optics, for example in the form of microlenses and beam splitters, which can be coupled to fibers ("fiber pig-tailed").

A "lead" is a conductive structure, typically an electrically insulated coiled wire. The electrically conductive material can be any conductive material, with metals and intermetallic alloys common. The outer sheath of insulative material is biocompatible and biostable (e.g., non-dissolving in the body) and generally includes organic materials such as polyurethane and polyimide. Lead types include, by way of non-limiting example, epicardial and endocardial leads. Leads are commonly implanted into a body percutaneously or surgically.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

An optical fiber (or laser active fibre) is a flexible, transparent fiber made of an optically transmissive material, such as glass (silica) or plastic that functions as a waveguide, or "light pipe", to transmit light between the two ends of the fiber.

"Packing density", as used with reference to optical fibers, refers to the amount of cross sectional area encompassed by the optical fibers within a selected cross sectional area of a selected portion of a catheter.

A "surgical implant" is a medical device manufactured to replace a missing biological structure, support, stimulate, or treat a damaged biological structure, or enhance, stimulate, or treat an existing biological structure. Medical implants are man-made devices, in contrast to a transplant, which is a transplanted biomedical tissue. In some cases implants contain electronics, including, without limitation, artificial pacemaker, defibrillator, electrodes, and cochlear implants. Some implants are bioactive, including, without limitation, subcutaneous drug delivery devices in the form of implantable pills or drug-eluting stents.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 2:
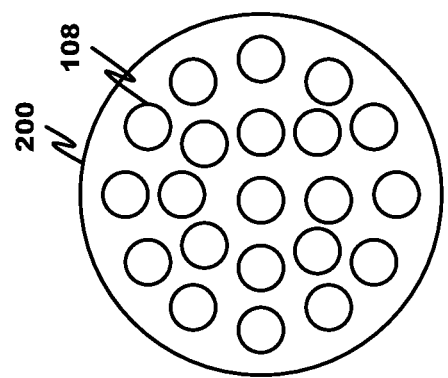
FIG. 2 is a front view of a distal end of a lumenless laser catheter assembly according to the prior art.
Figure 1:
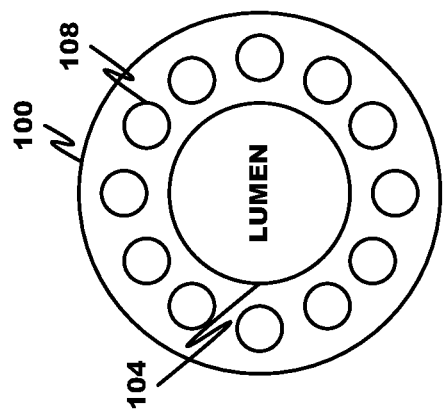
FIG. 1 is a front view of a distal end of a laser catheter assembly according to the prior art.

FIGS. 1 and 2 depict the working ends of various known prior art laser catheter assemblies having plural optical fibers 108 embedded therein. FIG. 1 shows a flexible catheter assembly 100 comprising a catheter lumen 104 to receive an implanted lead or guide wire (not shown) and plural laser emitters 108 positioned around the periphery or diameter of the catheter lumen 104. The "catheter assembly", as used herein, refers both to the catheter itself and the coupler to the laser. This type of catheter assembly is sold as a coronary laser atherectomy catheter by the Spectranetics Corporation under the tradenames ELCA™ and Turbo Elite™ (each of which is used for coronary intervention or catheterization such as recanalizing occluded arteries, changing lesion morphology, and facilitating stent placement) and as a laser sheath under the tradename SLSII™ and GlideLight™ (which is used for surgically implanted lead removal). FIG. 2 shows a flexible catheter assembly 200 comprising plural laser emitters 108 packed into the distal end of the catheter assembly. The number of rows of optical fibers and emitters located in the catheter assembly and/or located concentrically around the lumen and the number of optical fibers and emitters in each row can vary by application and are not limited to the depicted configurations. The primary difference between the catheter assemblies in FIGS. 1 and 2 is the absence of a catheter lumen 104 in the catheter assembly of FIG. 2.

Figure 4:
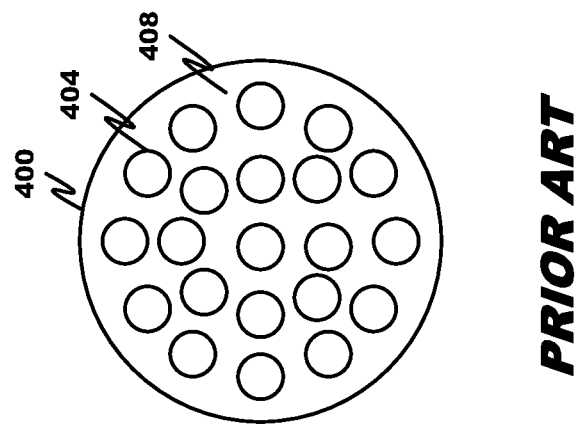
FIG. 4 is a front view of a proximal end of a laser catheter assembly according to the prior art.

FIG. 4 depicts a proximal end of a laser catheter adjacent to the coupler of a catheter assembly according to the prior art. An outer housing 400 of the proximal end or the distal end of the catheter surrounds the optical fibers 404, which are ultimately connected, or coupled, to the laser emitters 108. The catheter assembly couples to a laser, such as a low-temperature excimer laser (not shown) operating in the ultraviolet spectrum at around 308 nm. As can be seen, the circularly shaped optical fibers 404 are not closely or densely packed creating dead space 408 between the adjacent optical fibers 404. Commonly, the dead space 408, or space between the adjacent optical fibers, constitutes no more than about 50%, more commonly no more than about 30%, and even more commonly no more than about 25% of the cross-sectional area enclosed by the outer housing as depicted in FIG. 4.

Figure 8:
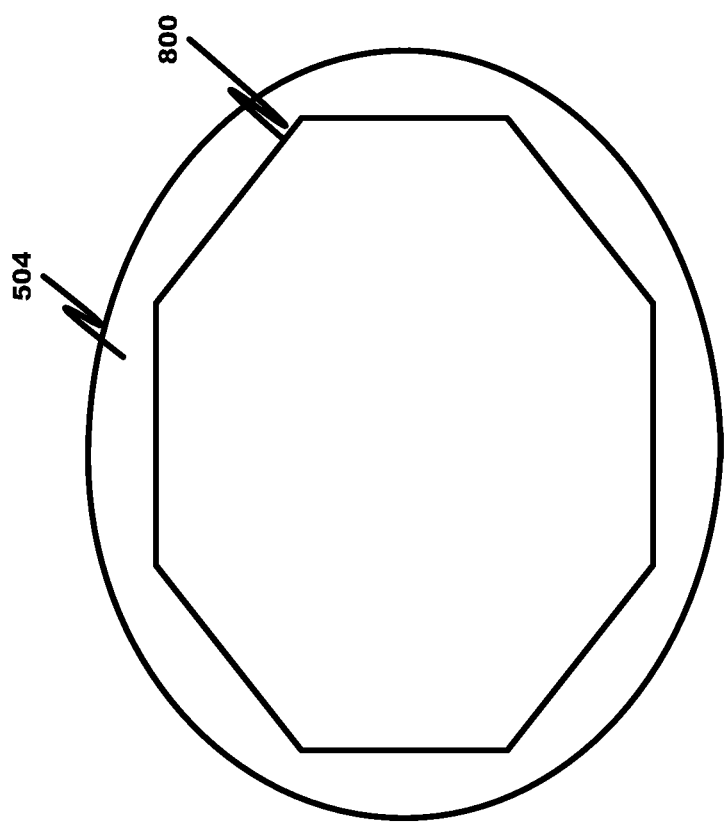
FIG. 8 is a front view of a prior art optical fiber.

FIG. 8 depicts an optical fiber according to the prior art. An octagonally shaped laser active core 800 is surrounded by a cladding material 504. The laser active core 800 is made of an optically transmissive material, such as doped or undoped fused silica. The cladding material 504 includes one or more cladding layers. Cladding is one or more layers of materials of lower refractive index, in intimate contact with the laser active core, or preform, material of higher refractive index. The cladding causes light to be confined to the core of the fiber by total internal reflection at the boundary between the two. Light propagation in the cladding is suppressed in a typical fiber. This causes the fiber to act as a waveguide. The normal thickness of the cladding material in circularly profiled fibers is at least about 2.5 microns and often ranges from about 2.5 to about 7.5 microns.

In one manufacturing process, silica is drawn into fibers, or preforms, at reasonably high temperatures. Silica, as will be appreciated, has a fairly broad glass transformation range. One purpose of doping is to raise the refractive index (e.g. with germanium dioxide ($GeO_2$) or aluminium oxide ($Al_2O_3$)) or to lower it (e.g. with fluorine or boron trioxide ($B_2O_3$)). Doping is also possible with laser-active ions (for example, rare earth-doped fibers) to obtain laser active fibers. Both the fiber core and cladding are typically doped, so that the entire assembly (core and cladding) is effectively the same compound (e.g. an aluminosilicate, germanosilicate, phosphosilicate or borosilicate glass). An exemplary optical fiber is manufactured by Heraeus Quarzglas GmbH & Co. KG.

Figure 3:
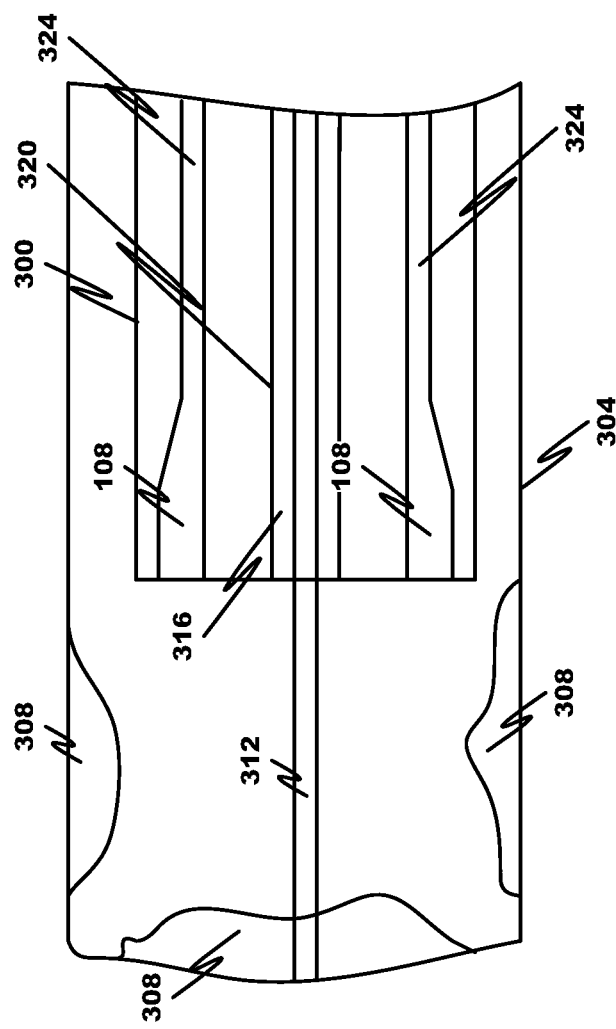
FIG. 3 is a side cross-sectional view of a laser catheter assembly positioned in a body lumen.

Referring to FIG. 3, a laser ablation catheter assembly 300 is positioned in a body lumen 304, such as a blood vessel, to remove a complete or partial occlusion 308. A guide wire 312 passes through the body lumen 304 and occlusion 308 on the one hand and the catheter lumen 316 formed by a substantially cylindrical inner catheter surface 320 on the other to guide the catheter assembly to the occlusion 308. Laser emitters 108 are positioned at the distal end of the catheter assembly to ablate the occlusion. Optical fiber 324 connects a corresponding emitter to the laser via the proximal end of the catheter and coupler (FIG. 4).

Figure 5B:
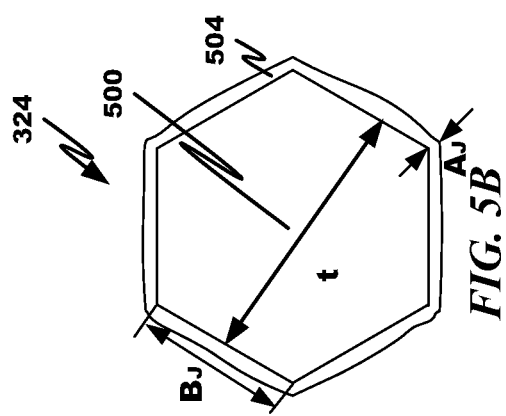
FIG. 5B is a front view of an angular optical fiber according to the present disclosure.
Figure 5A:
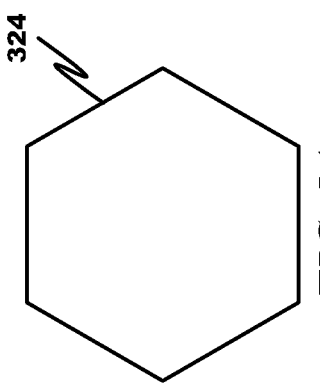
FIG. 5A is a front view of an angular laser active core of an optical fiber according to the present disclosure.

FIG. 5A depicts a non-circular or angular optical fiber configuration that can enable close or dense packing. This optical fiber 324 can be based, for example, on a hexagonal optical fiber preform, which is drawn down to the desired size. The optical fiber, in cross-section, is substantially hexagonally shaped, having plural substantially planar surfaces separated by angles. This configuration can gain optical fiber active area and reduce dead space between fibers by enabling dense stacking hexagonally shaped fibers in the catheter assembly.

FIG. 5B depicts additional details regarding the optical fiber 324 configuration of FIG. 5A. The laser active core 500 of the fiber has width "t" between opposing sides and is surrounded by one or more layers of cladding material 504 having a thickness $A_J$. The cladding material 504 includes pump cladding (which guides and couples pump light into the active core) and/or outer cladding. The length of each of the opposing sides is $B_J$.

The thickness of the outer cladding material 504 varies depending on location. Generally, the thickness $A_J$ is generally thinnest adjacent to a corner and thickest along the planar edges of the laser active core 500. The mode distribution will vary along the length of the fiber due to the non-circular outer cladding shape. Guiding losses are generally greatest at or near the corners of the laser active core; therefore, the minimum cladding thickness is generally maintained or exceeded adjacent to the laser active core corners.

Commonly, the thickness "t" (or flat-to-flat thickness) of the laser active core 500 varies from about 50 to about 200 microns and even more commonly from about 75 to about 150 microns while the thickness $A_J$ of the cladding material at or adjacent to the corners of the laser active core and/or of the optical fiber generally has a thickness of at least about 1 micron but no more than about 10 microns and even more generally of at least about 2 microns but no more than about 5 microns.

Figure 6B:
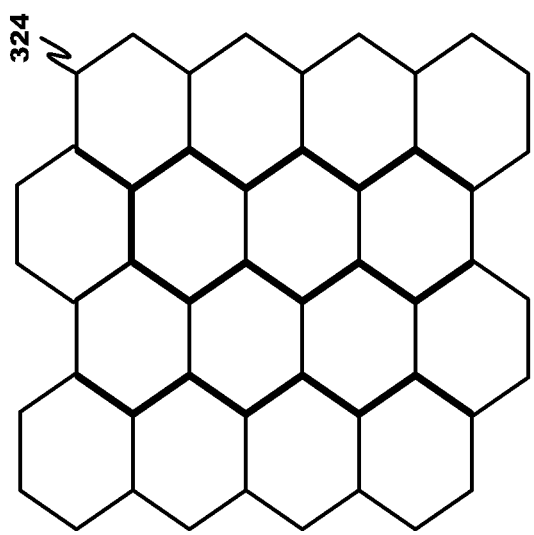
FIG. 6B is a front view of plural optical fibers according to the prior art.
Figure 6A:
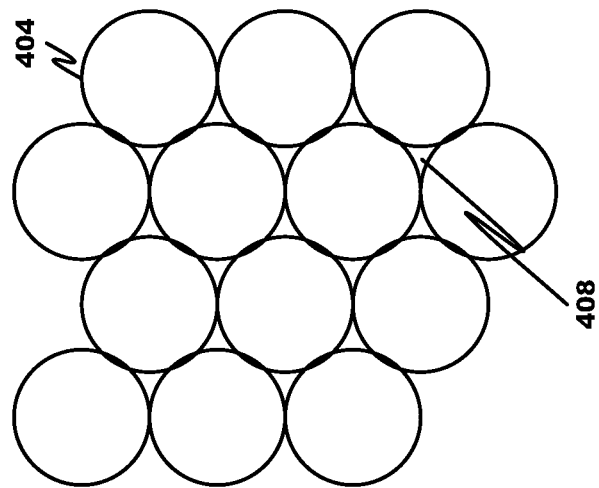
FIG. 6A is a front view of plural optical fibers according to the present disclosure.

FIGS. 6A and 6B depict the improved packing density in the proximal (e.g., adjacent to the coupler) end of the lumen or lumenless laser catheter assemblies and/or distal end of the lumenless laser catheter assembly using non-circular optic fibers. As can be seen from FIG. 6A, the substantially planar surfaces of the fibers 324 enable relatively close packing with little intervening dead space. In contrast, the packing density of prior art circular fibers 404 is less dense and consequently, substantially lower than optical fibers having planar surfaces. Typically, the packing density of the angular fibers 324 is at more than 50%, more typically at least about 80%, more typically at least about 85%, and even more typically at least about 90%. The packing density of the angular fibers 324 is thus greater than the packing density of circular fibers 404.

Figure 7A:
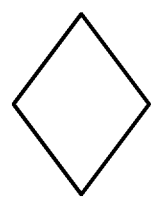
FIGS. 7A-H are front views depicting various angular optical fibers according to the present disclosure.
Figure 7B:
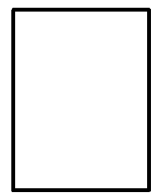
Figure 7C:
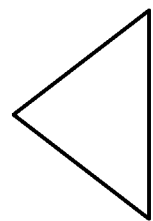
Figure 7D:
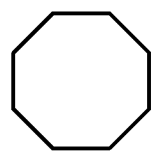
Figure 7E:
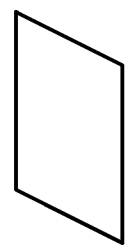
Figure 7F:
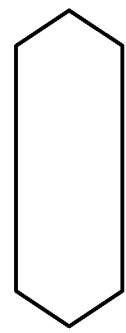
Figure 7G:
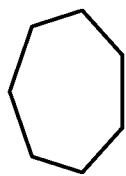
Figure 7H:
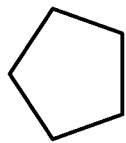

Other non-circular optical fiber configurations are envisioned by this disclosure. Examples include a diamond (FIG. 7A), a rectangle (FIG. 7B), a triangle (FIG. 7C), an octagon (FIG. 7D), a parallelogram (FIG. 7E), an elongated hexagon (FIG. 7F), a heptagon (FIG. 7G), and a pentagon (FIG. 7H).

A number of variations and modifications of the disclosure can be used. It would be possible to provide for some features of the disclosure without providing others.

For example in other alternative embodiments, innumerable other angular or substantially planar optical fiber configurations may be employed to realize relatively high levels of packing density in the proximal or distal ends of the laser catheter assembly.

The present disclosure, in various aspects, embodiments, and configurations, includes components, methods, processes, systems and/or apparatus substantially as depicted and described herein, including various aspects, embodiments, configurations, subcombinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A laser catheter assembly, comprising:
   a lumen for receiving at least one of a guide wire and a surgically implanted object;
   a plurality of laser active fibers disposed about the lumen, wherein each of the laser active fibers comprises:
   a fiber core having a hexagonal cross-section that is substantially non-circular and non-arcuate, wherein the hexagonal cross-section comprises at least three substantially planar edges having substantially angular corners therebetween; and
   a separate cladding material surrounding the fiber core, wherein the cladding material has a non-circular cross-section, and wherein the cladding material has a variable thickness about the fiber core so that the cladding material exhibits a first thickness along the planar edges of the core, and a second thickness adjacent to the substantially angular corners, wherein the second thickness is thinner than the first thickness but maintains a minimum cladding thickness of at least about 2 microns,
   wherein the plurality of laser active fibers are positioned adjacent to one another in a substantially circular arrangement about the lumen such that the cladding adjacent to one of the planar edges of one laser active fiber abuts the cladding adjacent to one of the planar edges of another laser active fiber, and
   wherein a packing density of the plurality of laser active fibers is at least 80%.

2. The laser catheter assembly of claim 1, wherein a laser active core of the fiber has a flat-to-flat thickness ranging from 50 to 200 microns.

3. A method, comprising:
   assembling a plurality of laser active fibers to provide a laser catheter assembly, the laser catheter assembly comprising a lumen for receiving at least one of a guide wire and a surgically implanted object, wherein the assembled laser active fibers are disposed about the lumen, and wherein each of the assembled laser active fibers comprises:
   a fiber core having a non-circular and non-arcuate cross-section, wherein the cross-section comprises at least three planar edges having substantially angular corners therebetween; and
   a separate cladding material surrounding the fiber core, wherein the cladding material has a hexagonal cross-section, and wherein the cladding material has a variable thickness about the fiber core so that the cladding material exhibits a first thickness along the planar edges, and a second thickness adjacent to the substantially angular corners, wherein the second thickness is thinner than the first thickness but maintains a minimum cladding thickness of at least about 2 microns,
   wherein a majority of the plurality of laser active fibers are positioned adjacent to one another such that the cladding adjacent to one of the planar edges of one laser active fiber abuts the cladding adjacent to one of the planar edges of another laser active fiber so that the plurality of laser active fibers collectively encircle the lumen, and
   wherein a packing density of the plurality of laser active fibers about the lumen is at least 80%.

4. A laser assembly manufactured by the method of claim 3.

5. A laser catheter assembly, comprising:
   a catheter body having an internal lumen extending therethrough; and
   a plurality of laser active fibers disposed in a circular arrangement about the internal lumen, wherein each of the laser active fibers comprises:
   a fiber core having a hexagonal cross-section with six planar edges having angular corners therebetween; and
   a separate cladding material surrounding the fiber core, wherein the cladding material has a non-circular cross-section having a variable thickness about the fiber core so that the cladding exhibits a first thickness along the planar edges, and a second thickness adjacent to the angular corners, wherein the second thickness is thinner than the first thickness but maintains a minimum cladding thickness of at least about 2 microns,
   wherein a majority of the plurality of laser active fibers are positioned adjacent to one another in the circular arrangement about the internal lumen such that the cladding adjacent to one of the planar edge of one laser active fiber abuts the cladding adjacent to one of the planar edge of another laser active fiber,
   wherein a packing density of the plurality of laser active fibers is at least 80%.

6. The laser catheter assembly of claim 5, wherein a laser active core of the fiber has a flat-to-flat thickness ranging from 50 to 200 microns.

7. The laser catheter assembly of claim 5, further comprising a lumen for receiving at least one of a guide wire and a surgically implanted object.

8. The laser catheter assembly of claim 5, wherein the second thickness is between 2.0 microns and 7.5 microns.

* * * * *